United States Patent [19]

Brake et al.

[11] Patent Number: 4,914,026

[45] Date of Patent: Apr. 3, 1990

[54] ALPHA FACTOR LEADER SEQUENCE DIRECTED SECRETION OF INSULIN

[75] Inventors: Anthony J. Brake, Berkeley; Lawrence S. Cousens, San Francisco; Mickey S. Urdea, San Francisco; Pablo D. T. Valenzuela, San Francisco, all of Calif.

[73] Assignee: Chiron Corporation, Emeryville, Calif.

[21] Appl. No.: 922,288

[22] Filed: Oct. 23, 1986

Related U.S. Application Data

[63] Continuation of Ser. No. 483,023, Apr. 7, 1983, abandoned.

[51] Int. Cl.$^4$ .................. C12P 21/00; C12P 21/02; C12N 15/00; C12N 5/00
[52] U.S. Cl. .................. 435/69.4; 435/172.3; 435/255; 935/11; 935/47; 935/48; 935/49; 935/13; 935/28; 935/37; 935/69; 536/27
[58] Field of Search ............... 435/68, 70, 172.3, 255, 435/256, 320; 935/11, 28, 37, 69, 79, 47, 48, 49; 536/27

[56] References Cited

U.S. PATENT DOCUMENTS 4,338,397  7/1982  Gilbert et al. .................. 435/68
4,431,740  2/1984  Bell et al. ...................... 435/253
4,546,082 10/1985  Kurjan et al. .................. 435/68

OTHER PUBLICATIONS

Bennetzen et al., *J. Biol Chem.* vol. 257(6) Mar.-25-82 "Codon Secretion in Yeast".
Hitzeman et al., *Science* vol. 219, pp. 620-625 Feb. 11, 1983 "Secretion of Human Interfemms by Yeast".

*Primary Examiner*—Robin Teskin
*Attorney, Agent, or Firm*—Irell & Manella

[57] ABSTRACT

Methods and compositions are provided for efficient production of polypeptides having insulin activity. The proinsulin gene is joined to secretion and processing signals for expression and secretion in yeast. The product may be obtained in enhanced yield in the nutrient medium.

Cell line AB103(PYinsl) was deposited at the A.T.C.C. on Apr. 6, 1983 and given Accession No. 20,670.

15 Claims, No Drawings

ALPHA FACTOR LEADER SEQUENCE DIRECTED SECRETION OF INSULIN

This application is a continuation of application Ser. No. 483,023, filed Apr. 7, 1983.

BACKGROUND OF THE INVENTION

1. Field of the Invention

Hybrid DNA technology permits the transcription and translation of genes to produce desired polypeptide products. For the most part, the polypeptide products that are of interest are associated with mammalian genes, while the choice of host cells has been primarily directed to prokaryotes and lower eukaryotes, e.g. fungi, especially yeast due to ease of propagation and genetic manipulation. In developing a methodology for producing DNA constructs which provide efficient production of a desired polypeptide, one must develop a protocol which allows for the insertion and excision of DNA fragments in an ordered way. Frequently, the various regulatory signals, replication system, markers and the structural gene(s) of interest will come from diverse sources. Therefore, one must develop a strategy which allows for endonuclease cleavages, insertions and excisions in an appropriate sequence, which provides for the DNA fragments being aligned in the correct orientation and the propr spatial relationship. Furthermore, the presence of sequences which do or could interfere with the efficient transcription, translation or propagation of the desired structural gene, must be avoided or may be present only where they do not have a detrimental effect.

In addition to the strategy involved with the preparation of the DNA construct, there is also the considerations of the choice of sequences which encode for the regulatory signals and expression products, their individual interactions, their effect on the host, the efficiency with which the energy of the host is diverted to the production of the desired polypeptide, and the ease of isolation of the polypeptide product. Therefore, each development of a process for the production of a particular polypeptide becomes an intellectual exercise in experimental design, procedural organization, and investigation.

2. Description of the Prior Art

The human DNA sequence for human insulin may be found in Bell et al., *Nature* (1979) 282: 525–527. Production of rat "pre"-proinsulin polypeptide fragments in bacteria is described in U.S. Pat. No. 4,338,397. Kurjan and Herskowitz, *Cell* (1982) 30: 933–943 describe a putative α-factor precursor containing four tandem copies of mature α-factor, describing the sequence and postulating a processing mechanism. Kurjan and Herskowitz, Abstracts of Papers presented at the 1981 Cold Spring Harbor Meeting on The Molecular Biology of Yeast, p. 242, in an Abstract entitled, "A Putative Alpha-Factor Precursor Containing Four Tandem Repeats of Mature Alpha-Factor," describe the sequence encoding for the α-factor and spacers between two of such sequences. U.S. Pat. No. 4,338,397, col. 3 and 4, provides for useful definitions, which definitions are incorporated herein by reference.

SUMMARY OF THE INVENTION

Method and compositions are provided for the production of a "pre"-proinsulin in a yeast host and secretion of processed "pre"-proinsulin into the nutrient medium. The DNA constructs are produced by joining of DNA sequences from diverse sources, providing a construct which is stably replicated in a yeast host and results in efficient high level production of processed "pre"-proinsulin into the nutrient medium, where it may be isolated in high yield.

DESCRIPTION OF SPECIFIC EMBODIMENTS

Novel DNA constructs are provided for the efficient production of mammalian "pre"-proinsulin in a yeast hose and processing for the "pre"-proinsulin. The constructs provide for transcription and translation of mammalian "pre"-proinsulin and processing and secretion of the polypeptide product into the nutrient medium. The construction therefore involves a DNA construct which includes a replication system capable of stable maintenance in a yeast host; an efficient promoter; a structural gene including leader and processing signals joined to the coding region for proinsulin in reading frame with the secretion leader and processing coding sequence, and a terminator sequence downstream from the structural gene. Optionally, other sequences can be provided for transcriptional regulation, amplification of the gene, exogenous regulation of transcription, and the like.

The "pre"-proinsulin intends a gene encoding for human proinsulin in reading frame with a leader sequence and processing signals efficiently recognized by the yeast host. Thus, "pre" intends the secretion and processing signals associated with the yeast host as distinguished from the human sequences naturally present with proinsulin for processing the native prepropeptide to proinsulin.

In preparing the construct, it is necessary to bring the individual sequences together in a predetermined order to ensure that at each stage, sequences which are present are not disturbed, so as to detrimentally affect their function, and that each of the sequences which are introduced are properly positioned in relation to the other sequences, so as to be able to fulfill their individual functions. Furthermore, adaptor molecules may be employed to advantage for organizing the construct.

The proinsulin gene which is employed may be chromosomal DNA, cDNA, synthetic, or combinations thereof. Since the proinsulin gene is a mammalian gene and the regulatory, leader and processing, and transcriptional terminator signals will be sequences derived from and recognized by the host, it will be useful to join the several sequences by means of connecting or adaptor sequences. Thus, by appropriate choice of restriction sites, one can provide the proinsulin gene restricted internally and proximal to the 5'-terminus of the coding strand, so as to lack a number of base pairs. Similarly, the leader and processing signal sequences may be restricted internal and proximal to the 3'-terminus of the coding strand, so as to lack a plurality of base pairs. (Unless otherwise indicated, the 5'- and 3'- designations intend the coding strand.) The restriction sites are chosen so that the adaptor results in the proper reading frame for the proinsulin gene.

Since the adaptor can be prepared synthetically, it is desirable that the codons of the adaptor be those preferentially utilized by the yeast host, e.g. as occur in glycolytic enzymes, rather than employing the naturally occurring mammalian codons. The adaptor will have from about 20 to 40, more usually from about 25 to 35 bases in the coding sequence and may have cohesive ends or butt ends, preferably cohesive ends. Desirably, the termini of the adaptor will have different cohesive ends, so as to ensure the proper orientation of the adaptor. Therefore, the two ends to be linked will also have different termini.

For the leader and processing signals, one may use a naturally occurring DNA sequence from yeast. Polypeptides which are secreted by yeast include α-factor, a-factor, and the like.

The subject invention will be illustrated with the cDNA gene for proinsulin used with the regulatory, leader and processing signals, and transcriptional terminator of yeast α-factor.

The yeast α-factor may be restricted with HindIII and SalI. HindIII cleaves in the processing signal of the α-factor, cleaving at the second base in the coding strand of the glu codon, while the recognition sequence completes the glu codon and encodes for ala. The SalI site is prior to the α-factor transcriptional terminator.

The human proinsulin cDNA is restricted with EcoRI to provide a fragment (EcoRI-EcoRI) having a complete coding sequence for proinsulin, as well as flanking sequences. By partially digesting the EcoRI-EcoRI fragment with EcoRII, cleaving internal to the coding sequence, a truncated fragment is obtained lacking a portion of the coding sequence at the 5'-terminus. The last base pairs may be provided by an adaptor, which will join the leader and processing signal fragment (HindIII site) with the EcoRII-EcoRI fragment in proper reading frame. The adaptor may be produced as a single fragment or may be produced by joining two or more single strands together. The adaptor recreates the necessary codons of the processing signal and gene to be expressed.

At the other end of the fragment containing the cDNA gene for proinsulin is the EcoRI recognition sequence. The α-factor gene has a SalI restriction site at base 533 from the first base of the f-met codon. A small EcoRI-SalI adaptor serves to join the two ends in this 3'-non-coding region and thus serves to restore the α-factor transcriptional terminator to the construct.

Conveniently, the promoter which is employed may be the promoter associated with the leader sequence. In this manner, one can provide a 5'-portable element which contains both the promoter and the leader sequence in proper spatial relationship for efficient transcription. One may further include a transcriptional terminator to create a "cassette" consisting of: promoter/leader—heterologous gene—terminator. This is achieved by isolating a DNA fragment which includes an intact gene from a yeast host and the upstream and downstream transcriptional regulatory sequences of the gene, where the gene expresses a polypeptide which is secreted by a yeast host. This has been exemplified above with α-factor.

The proinsulin cDNA will have its own stop codons to ensure that the C-terminus of the polypeptide is the same as the naturally occurring C-terminus.

Alternatively, one may replace the naturally occurring promoter by other promoters which allow for transcriptional regulation. This will require sequencing and/or restriction mapping of the region upstream from the leader sequence to provide for introduction of a different promoter. In some instances, it may be desirable to retain the naturally occurring promoter and provide a second promoter in tandem, either upstream or downstream from the naturally occurring promoter.

A wide variety of promoters are available or can be obtained from yeast genes. Promoters of particular interest include those promoters involved with enzymes in the glycolytic pathway, such as promoters for alcohol dehydrogenase, glyceraldehyde-3-phosphate dehydrogenase, pyruvate kinase, triose phosphate isomerase, phosphoglucoisomerase, phosphofructokinase, etc. By employing these promoters with regulatory sequences, such as operators, repressors and derepressors, and using a host having an intact regulatory system, one can regulate the expression of the processed "pre"-proinsulin. Thus, various small organic molecules, e.g. glucose, may be employed for the regulation of production of the desired polypeptide.

One may also employ temperature-sensitive regulatory mutants which allow for modulation of transcription by varying the temperature. Thus, by growing the cells at the non-permissive temperature, one can grow the cells to high density, before changing the temperature in order to provide for expression of the processed "pre"-proinsulin.

Other capabilities may also be introduced into the construct. For example, some genes provide for amplification, where upon stress to the host, not only is the gene which responds to the stress amplified, but also flanking regions. By placing such a gene upstream from the promoter and the other regulatory signals providing transcriptional control of the "pre"-proinsulin, and stressing the yeast host, plasmids may be obtained which have a plurality of repeating sequences, which sequences include the "pre"-proinsulin gene with its regulatory sequences. Illustrative genes include metallothioneins and dihydrofolate reductase.

The construct may include in addition to the leader sequence fragment, other DNA homologous to the host genome. If it is desired that there be integration of the proinsulin gene into the chromosome(s), integration can be enhanced by providing for sequences flanking the proinsulin gene construct which are homologous to host chromosomal DNA.

The replication system which is employed will be recognized by the yeast host. Therefore, it is desirable that the replication system be native to the yeast host. A number of yeast vectors are reported by Botstein et al., *Gene* (1979) 8:17-24. Of particular interest are the YEp plasmids, which contain the 2 μm plasmid replication system. These plasmids are stably maintained at multiple copy number. Alternatively or in addition, one may use a combination of ARS1 and CEN4, to provide for stable maintenance.

After each manipulation, as appropriate, the construct may be cloned so that the desired construct is obtained pure and in sufficient amount for further manipulation. Desirably, a shuttle vector (i.e., containing both a yeast and bacterial origin or replication) may be employed so that cloning can be performed in prokaryotes, particularly *E. coli*.

The plasmids may be introduced into the yeast host by any convenient means, employing yeast host cells or spheroplasts and using calcium precipitated DNA for transformation or other conventional techniques. The modified hosts may be selected in accordance with the genetic markers which are usually provided in a vector used to construct the expression plasmid. An auxotrophic host may be employed, where the plasmid has a gene which complements the host and provides prototrophy. Alternatively, resistance to an appropriate biocide, e.g. antibiotic, heavy metal, toxin, or the like, may be included as a marker in the plasmid. Selection may then be achieved by employing a nutrient medium which stresses the parent cells, so as to select for the cells containing the plasmid. The plasmid containing cells may then be grown in an appropriate nutrient medium, and the desired secreted polypeptide isolated in accordance with the conventional techniques. The polypeptide may be purified by chromatography, extraction, etc. Since the polypeptide will be present in mature form in the nutrient medium, one can cycle the nutrient medium, continuously removing the desired polypeptide.

The following examples are offered by way of illustration and not by way of limitation.

EXPERIMENTAL

1. EcoRI digestion of phins 1-19

(~700 μg) phins 1-19 (517 bp cDNA containing the entire human proinsulin gene, cloned in the EcoRI site of pBR328) was incubated with ~1600 units of EcoRI (New England Biolabs) in one ml at 37° C. for approximately 4.5 h (until completion) under the buffer conditions prescribed by the manufacturer. (phins 1-19 is derived from the plasmid described by Bell et al., supra, by PstI cleavage, Bal31 resection, attachment of EcoRI linkers and insertion into pBR328).

Isolation of EcoRI-EcoRI fragment of phins 1-19 containing human proinsulin gene The EcoRI-EcoRI fragment was isolated by 5% non-denaturing polyacrylamide gel electrophoresis. The gel was stained in a solution of 1 μg/ml ethidium bromide for approximately 10 min, and visualized under long wavelength UV light. The band corresponding to the 517 bp fragment was cut out and isolated from the gel by electroelution (Smith, *Methods in Enz.* (1980) 65: 371–380). The DNA was concentrated and purified by passing it through an Elutip-d column (Schleicher and Schuell Inc.) under the prescribed conditions.

2. Partial digestion of EcoRI-EcoRI piece with EcoRII

The EcoRI-EcoRI fragment (~17 μg) was incubated with ~3 units of EcoRII (Bethesda Research Labs) in a volume of 170 μl at 37° C. under the prescribed buffer conditions. Aliquots of equal volume were removed at 18, 21 and 25 min.

Isolation of the EcoRII-EcoRI piece (long fragment)

The 329 bp EcoRII-EcoRI fragment was isolated by polyacrylamide gel electrophoresis, followed by electroelution and Elutip-d chromatography as described above.

3. Ligation of EcoRII-EcoRI fragment to synthetic fragments

The EcoRII to EcoRI partial digest fragment containing most of the insulin coding region was evaporated to dryness from water (80 μg, 0.35 picomoles) in a siliconized 1.5 ml Eppendorf tube. To the pellet, 10 picomoles of the 5'-phosphorylated synthetic fragments 3 and 4 and 25 picomoles of 2 and 5 were added to bring the volume to 14 μl. Fragments 2–5 had the following DNA sequences (indicated 5'→3'):

2. ACAAAAGCTTC
3. TTGTGAACCAACACCTGTGCGGCTCACA
4. CCAGGTGTGAGCCGCACAGGTGTTGGTTC
5. AATTTGATAAG

To this was added 5 μg of poly-A (5 μl), 250 mM EDTA (1 μl), 2M sodium acetate (20 μl). The solution was heated to 60° C. for 5 min to inactive residual kinase and then 25 picomoles of the 5'-hydroxy synthetic fragments 1 and 6 were added. Fragments 1 and 6 had the following DNA sequences:

1. AGCTGAAGCTT
6. TCGACTTATCA

This protocol thus prevents concatemer formation. These fragments bridge the codons from the yeast α-factor processing signals to the EcoRII restriction site in proinsulin at the codons for his or leu and also provide the adaptor bridging the EcoRI restriction site of the proinsulin gene-containing fragment and the SalI restriction site of the fragment containing the yeast α-factor, where both the EcoRI and salI sites are downstream from their respective coding regions.

The mixture was vortexed, 200 μl of 95% ethanol was added and the DNA was precipitated by holding the tube at −80° C. for 20 min. After centrifugation for 10 min at 12,800 G, the solution was decanted, washed with cold ethanol and evaporated to dryness. Annealing of the fragments was achieved by adding 8 μl of water, vortexing, heating to 90° C. and cooling to 14° C. over a 1 h period. The solution was adjusted to contain 50 mM Tris-HCl (pH 7.8), 10 mM MgCl₂, 1 mg/ml spermidine, 10 mM dithiothreitol, 1 mM ATP (ligation buffer) in a total volume of 27 μl.

Ligation was initiated by the addition of 6 Weiss unit of T4 DNA ligase (3 μl). After 2h at 14° C. the anticipated 433 bp HindIII to SalI fragment was isolated by 7% polyacrylamide gel electrophoresis under non-denaturing conditions. The band was visualized by staining with ethidium bromide (0.5 μg/ml), cut out, and electroeluted. The contents of the bag were removed, 5 μg of poly-A was added, the DNA ethanol precipitated and dried. The fragment was 5'-phosphorylated with T4 polynucleotide kinase (3 units) at 37° C. for 1 h in a total of 20 μl of the ligation buffer.

4. Ligation of the HindIII-SalI α-factor-proinsulin fusion fragment into pAB113 pAB113 is a plasmid comprising a 1.8 kb EcoRI fragment containing the yeast α-factor gene cloned in the EcoRI site of pBR322 in which the HindIII and SalI sites have been deleted. pAB113 is derived from plasmid pAB101, which contains the yeast α-factor gene as a partial Sau3A fragment cloned in the BamHI site of plasmid YEp24. pAB101 is obtained by screening a yeast genomic library cloned in YEp24 using a synthetic oligonucleotide probe homologous to the published α-factor coding region (Kurjan and Herskowitz, Abstracts 1981 Cold Spring Harbor Meeting on the Molecular Biology of Yeasts, p. 242). pAB113 was completely digested with endonucleases HindIII and SalI.

The sample containing the ligation product prepared above was heated to 60° C. and 100 ng of the digested pAB113 was added. The solution was cooled to 14° C. over a 15 min period, 2 Weiss units of T4 ligase were added, and the ligation was conducted for 2 h at 14° C.

Transformation of *E. coli* HB101 with pAB113 containing the insert and testing transformants After ethanol precipitation, the pellet was taken up in 75 mM CaCl₂ and used to transform competent *E. coli* HB101 cells.

Eight transformants were obtained, from each of which plasmid DNA was extracted (Birboim and Doly, *J. Nuc. Acids Res.* (1979) 7: 1513. The recombinant plasmids were digested with PstI and SalI and then electrophoretically examined for yield of the anticipated fragments of 319, 207, 79, 48, 31 and 27 bp characteristic of the α-factor-proinsulin insert. Five of the eight transformants, indicated as pyins -1, -2, -3, -4, -5 contained the α-factor-proinsulin insert. Preparations of plasmid DNA from one liter cultures were made for each of the positive transformants.

5. EcoRI digestion of pyins -1, -2, -3, -4, -5

Plasmid DNA (140 μg) from each of the transformants was incubated for 4 h with 240 units of EcoRI (BRL) in a volume of 200 μl under prescribed buffer conditions.

Isolation of the EcoRI-EcoRI fragment

The 2056 bp EcoRI-EcoRI fragment was isolated by 5% polyacrylamide electrophoresis (alternatively, agarose could be used). The gel was stained with ethidium bromide, and the anticipated UV-visualized band was excited. The DNA was isolated by electroelution and purified by chromatography as described above.

6. Ligation of EcoRI-to-BamHI adaptor molecules onto EcoRI-EcoRI fragment

Each "pyin" clone (~4 μg) was incubated with 1.0 μg of the 5'-phosphorylated EcoRI-to-BamHI adaptors of the following DNA sequences in the presence of 2000 units of T4 DNA ligase (New England Biolabs).
5'-GATCCCTCTAGG-3' and 5'-AATTC-CTAGAGG-3'
The reaction was conducted in a volume of 900 μl of the prescribed buffer for 2.5 h at 18° C. The sample was heated to 65° C. for 10 min, phenol extracted, and digested with 100 units of BamHI (BRL) in 250 μl of the prescribed buffer at 37° C. for 4 h.

The BamHI-BamHI α-factor-proinsulin fragment was purified by 1% agarose gel electrophoresis, followed by electroelution and subsequent column chromatography as above.

7. Ligation of BamHI-BamHI fragment into the BamHI site of pC1/1

The BamHI-BamHI fragment of pyins-1 (0.7 μg) and 0.4 μg of the same fragment from the other "pyins" clones were ligated to a quantity of BamHI-digested pC1/1 corresponding to a mole ratio of 10 fragments:1 vector. (Plasmid pC1/1 is a derivative of pJDB219 (Beggs, Nature (1978) 275: 104) in which the region corresponding to bacterial plasmid pMB9 in pJDB219 has been replaced by pBR322 in pC1/1. pC1/1 contains a complete 2 μm replicator, yeast LEU2 gene and complete pBR322.) All the ligations were done with a DNA concentration of 5 μg/ml and 800 units of T4 ligase (New England Biolabs) for 2.5 h at 21° C.

After ethanol precipitation, the DNA was resuspended in 100 μl of 75 mM CaCl₂ and used to transform competent E. coli HB101 cells.

Testing of transformants for the presence of the α-factor-proinsulin insert

Hundreds of transformants were obtained for each "pyins" clone. Four transformants from each of the five "pyins" clones were tested by extracting the plasmid DNA and digesting it with PstI (New England Biolabs) which would yield anticipated characteristic fragments of 207, 48 and 27 bp in the presence of the insert. Fourteen of the 20 transformants tested were found to contain the α-factor-proinsulin insert, each of the original "pyins" clones being represented. Plasmid preparations were made of a transformant from each of the original "pyins" clones.

The plasmids were employed to transform yeast AB103 cells (α, pep 4-3, leu 2-3, leu 2-112, ura 3-52, his 4-580) and Leu+ transformants selected.

Insulin radioimmunoassay of cell medium

The yeast transformants, AB103 (pYins1 or pYins5) were grown as "patches" on a minimal plate without leucine. A sterile plastic inoculating loop was used to remove some of each patch into 2 ml of minimal medium without leucine. The cultures, and a control culture of AB103(pC1/1) were grown to saturation. The cells were pelleted by centrifugation for 10 min at 2,500 rpm in a Beckman J6B centrifuge. The supernatant was removed for RIA assay using a kit supplied by Amersham. One, 10 and 100 μl of supernatant were assayed.

| Expt | Clone | Conc "Insulin" (ng/ml) |
|---|---|---|
| 1 | pC1/1 | 0 |
|  | pYins5-2B | 16 |
|  | pYins5-3A | 13 |
|  | pYins5-3B | 33 |
| 2 | pC1/1 | 0 |
|  | pYins1-4A | 60 |
|  | pYins5-2B | 32 |
|  | pYins5-3B | 22 |
|  | pYins7-1A | 15 |
|  | pYins7-2A | 46 |
|  | pYins8-4 | 48 |

In a lipogenesis bioassay (Moody et al., Horm. Metab. Res. (1974) 6:12–16), a 1 μg sample showed 27% of the activity of insulin. The sample was obtained from the plasmid pYins1-4A as follows: For this characterization the yeast culture was centrifuged to remove cells and the supernatant medium acidified to pH 3 with acetic acid. The material was then purified by absorption to Biorex-70; the column was washed with 0.1N acetic acid and 50% ethanol and the material then eluted with 10 mM HCl in 80% ethanol. The eluate was taken to dryness by rotary evaporation and taken up in a small volume of water. The above result demonstrates the presence of an insulin active polypeptide.

In accordance with the subject invention, novel constructs are provided which may be inserted into vectors to provide for expression of "pre"-proinsulin to provide processing and secretion. Thus, one can obtain a polypeptide having the identical sequence to the naturally occurring human insulin. By virtue of providing for secretion, greatly enhanced yields can be obtained based on cell population and subsequent preparative operations and purification are simplified.

Although the foregoing invention has been described in some detail by way of illustration and example for purposes of clarity of understanding, it will be obvious that certain changes and modifications may be practiced within the scope of the appended claims.

What is claimed is:

1. An improved method for expressing "pre"-proinsulin in yeast resulting in processing and secretion of said "pre"-proinsulin, wherein said "pre" means the presence of yeast secretion signals, said method comprising:

1. 
   (a) providing a "pre"-proinsulin gene comprising a first DNA sequence encoding proinsulin and a second DNA sequence encoding a yeast alpha-factor leader sequence that provides for secretion from a Saccharomyces host, wherein the coding sequences of said first and second DNA sequences are in the same reading frame;
   (b) introducing said "pre"-proinsulin gene into an expression vector for a Saccharomyces host;
   (c) transforming a Saccharomyces host with said expression vector comprising said "pre"-proinsulin gene; and
   (d) growing said transformed Saccharomyes host in a nutrient medium under conditions whereby proinsulin is expressed and secreted.

2. A method according to claim 1 wherein said first DNA sequence comprises a human insulin cDNA fragment.

3. A method according to claim 1 wherein said expression vector comprises a replication system recognized by said Saccharomyces host.

4. A method according to claim 1 wherein said expression vector comprises a replication system recognized by E. coli.

5. A method comprising:
   (a) providing a Saccharomyces host transformed by an expression cassette comprising a heterologous gene comprising a first DNA sequence encoding a yeast alphafactor leader sequence that provides for secretion in reading frame with a second DNA sequence encoding proinsulin; and
   (b) growing said Saccharomyces host in a nutrient medium under conditions whereby said heterologous gene is expressed and secreted into said nutrient medium.

6. A method according to claim 5 wherein said second DNA sequence comprises a human insulin cDNA fragment.

7. A method according to claim 5 wherein said expression cassette is in a vector comprising a replication system recognized by said Saccharomyces host.

8. A method according to claim 5 wherein said expression cassette is in a vector comprising a replication system recognized by E. coli.

9. A method according to claim 7 wherein said replication system comprises a 2 micron plasmid sequence.

10. A DNA construct comprising a first DNA sequence encoding a yeast alpha-factor leader sequence that provides for secretion in reading frame with a second DNA sequence encoding proinsulin.

11. A DNA construct according to claim 10 further comprising a replication sysem recognized by Saccharomyces.

12. A DNA construct according to claim 11 wherein said replication system comprises a 2 micron plasmid sequence.

13. A DNA construct according to claim 10 further comprising a replication system recognized by E. coli.

14. A DNA construct according to claim 10 wherein said yeast is Saccharomyces.

15. In a method of producing a recombinant polypeptide wherein a microorganism is transformed by a recombinant DNA construct encoding a precursor of insulin and provides for the expression of said recombinant polypeptide; and said said microorganism is grown in a nutrient medium under conditions whereby said recombinant polypeptide is expressed, the improvement comprising employing Saccharomyces as said microorganism and said recombinant DNA construct encodes a yeast alpha-factor leader sequence that provides for secretion of mature insulin having insulin activity into said nutrient medium.

* * * * *